(12) United States Patent
Bryja et al.

(10) Patent No.: US 9,057,106 B2
(45) Date of Patent: Jun. 16, 2015

(54) METHOD OF DETERMINATION OF DIAGNOSIS AND PROGNOSIS IN PATIENTS WITH B-CELL CHRONIC LYMPHOCYTIC LEUKEMIA AND OLIGONUCLEOTIDES FOR USE IN THIS METHOD

(75) Inventors: Vitezslav Bryja, Brno (CZ); Pavel Krejci, Nove Mesto na Morave (CZ); Marketa Kaucka, Hradec Kralove (CZ); Sarka Pospisilova, Brno (CZ); Jiri Mayer, Brno (CZ); Alois Kozubik, Brno (CZ); Karla Plevova, Hostalkova u Vsetina (CZ); Jana Kotaskova, Brno (CZ)

(73) Assignee: MASARYKOVA UNIVERZITA, Brno (CZ)

( * ) Notice: Subject to any disclaimer, the term of this patent is extended or adjusted under 35 U.S.C. 154(b) by 146 days.

(21) Appl. No.: 13/388,438

(22) PCT Filed: Aug. 3, 2010

(86) PCT No.: PCT/CZ2010/000090
§ 371 (c)(1),
(2), (4) Date: Feb. 9, 2012

(87) PCT Pub. No.: WO2011/015162
PCT Pub. Date: Feb. 10, 2011

(65) Prior Publication Data
US 2012/0135419 A1   May 31, 2012

(30) Foreign Application Priority Data

Aug. 4, 2009   (CZ) .............................. PV 2009-518

(51) Int. Cl.
| | | |
|---|---|---|
| *G01N 33/53* | (2006.01) | |
| *G01N 33/68* | (2006.01) | |
| *G01N 33/574* | (2006.01) | |
| *G01N 33/577* | (2006.01) | |
| *C12Q 1/68* | (2006.01) | |
| *G01N 33/50* | (2006.01) | |

(52) U.S. Cl.
CPC .......... *C12Q 1/6886* (2013.01); *G01N 33/5052* (2013.01); *G01N 33/6842* (2013.01); *G01N 33/5091* (2013.01); *G01N 33/577* (2013.01); *G01N 33/57426* (2013.01); *C12Q 2600/118* (2013.01)

(58) Field of Classification Search
CPC .......... G01N 33/5052; G01N 33/5091; G01N 33/53; G01N 33/558; G01N 33/574; G01N 33/57426; G01N 33/577; G01N 33/6842

USPC .................................. 435/7.1, 7.2, 7.21, 7.23
See application file for complete search history.

(56) References Cited

U.S. PATENT DOCUMENTS

| | | | | |
|---|---|---|---|---|
| 7,459,280 B2* | 12/2008 | Wang et al. | .................. | 435/7.23 |
| 7,867,705 B2* | 1/2011 | Wands et al. | ................ | 435/6.16 |

OTHER PUBLICATIONS

Memarian et al. Variation in WNT genes expression in different subtypes of chronic lymphocytic leukemia. Leukemia & Lymphoma 2009;50(12):2061-70.*
Liang, H., et al., Cancer Cell, 4: 349-360, 2003.*
Katoh Masaru, WNT/PCP signaling pathway and human cancer, Onocology Reports, vol. 14, No. 6, Dec. 2005, p. 1583-1588, Spandidos Publications.
Mahadevan Daruka et al: "Gene Expression and Serum Cytokine Profiling of Low Stage CLL Identify WNT/PCP..." Human Genomics and Proteomics, vol. 2009, Jun. 2009, pp. 1-12.
Wang Z et al: "Amino acid limitation induces down-regulation of WNT5a at transcriptional level", Biochemical and Biophysical Research Communications, vol. 378, No. 4, Jan. 2009, pp. 789-794, Academic Press Inc., Orlando, FL.
Lu Desheng et al: "Activation of the Wnt signaling pathway in chronic lymphocytic leukemia", Proceedings of the National Academy of Sciences of the United States (PNAS), vol. 101, No. 9, Mar. 2004, pp. 3118-3123.

* cited by examiner

*Primary Examiner* — Misook Yu
*Assistant Examiner* — Anne Holleran
(74) *Attorney, Agent, or Firm* — Notaro, Michalos & Zaccaria P.C.

(57) ABSTRACT

The invention provides a method of determination of diagnosis and prognosis of B-cell chronic lymphocytic leukemia from a biological sample collected from the body of a patient, wherein the status of Wnt/PCP signaling pathway is determined. Within the framework of the present invention the relation of CLL and molecular signaling pathway Wnt/PCP the components of which are markedly up-regulated in B-lymphocytes of the patients suffering from CLL was identified. The status of the Wnt/PCP signaling pathway can be determined, e.g., by the determination of the expression of components of said signaling pathway or by the determination of migration of CLL cells in the gradient of a chemokine in the presence of the ligand of said signaling pathway. The invention also relates to suitable oligonucleotides for use in the method of determination of expression of the signaling pathway components.

3 Claims, 7 Drawing Sheets

B. Summary of protein expression analysis in peripheral blood mononuclear cells

|  | healthy controls | CLL (0-II) | CLL (III-IV) |
|---|---|---|---|
| Ror1 | 24/ 0 / 0 | 0 / 7 / 13 | 0/ 0 / 15 |
| Vang | 13 / 1 / 0 | 6 / 5 / 8 | 0 / 1 / 14 |
| Ck1e | 24 / 0 / 9 | 5/ 10 / 5 | 0 / 1 / 14 |
| Ck2a | 11/ 13 / 0 | 4 / 8 / 8 | 1 / 1 / 13 |
| Dvl2 | 20 / 2 / 0 | 4 / 9 / 7 | 0 / 1 / 11 |
| Dvl3 | 22/ 2 / 0 | 6 / 5 / 8 | 1 / 0 / 14 |

A. Wnt5a promotes migration of CLL cells in CXCL12 gradient

B. Key role of CK1 inhibition on migration of CLL cells

SEQUENCE LISTING

<160> NUMBER OF SEQ ID NOS: 12

<210> SEQ ID NO 1
<211> LENGTH: 22
<212> TYPE: DNA
<213> ORGANISM: Artificial
<220> FEATURE:
<223> OTHER INFORMATION: Forward primer

<400> SEQUENCE: 1
tacaaccttt gggctctggc tg                    22

```
<210> SEQ ID NO 2
<211> LENGTH: 22
<212> TYPE: DNA
<213> ORGANISM: Artificial
<220> FEATURE:
<223> OTHER INFORMATION: Forward primer

<400> SEQUENCE: 2
ttgaggatgt gccaagattt gc                                              22

<210> SEQ ID NO 3
<211> LENGTH: 21
<212> TYPE: DNA
<213> ORGANISM: Artificial
<220> FEATURE:
<223> OTHER INFORMATION: Forward primer

<400> SEQUENCE: 3
taccacggag agaagggcat c                                               21

<210> SEQ ID NO 4
<211> LENGTH: 22
<212> TYPE: DNA
<213> ORGANISM: Artificial
<220> FEATURE:
<223> OTHER INFORMATION: Forward primer

<400> SEQUENCE: 4
ttcagtgctc agcggaagaa ag                                              22

<210> SEQ ID NO 5
<211> LENGTH: 25
<212> TYPE: DNA
<213> ORGANISM: Artificial
<220> FEATURE:
<223> OTHER INFORMATION: Forward primer

<400> SEQUENCE: 5
acagtagtaa cgggcacctc agagc                                           25

<210> SEQ ID NO 6
<211> LENGTH: 19
<212> TYPE: DNA
<213> ORGANISM: Artificial
<220> FEATURE:
<223> OTHER INFORMATION: Forward primer

<400> SEQUENCE: 6
aacagccgct tcaactcgc                                                  19

<210> SEQ ID NO 7
<211> LENGTH: 22
<212> TYPE: DNA
<213> ORGANISM: Artificial
<220> FEATURE:
<223> OTHER INFORMATION: Reverse primer

<400> SEQUENCE: 7
ccttcatcag ggtcgttagc ac                                              22

<210> SEQ ID NO 8
<211> LENGTH: 23
<212> TYPE: DNA
<213> ORGANISM: Artificial
<220> FEATURE:
<223> OTHER INFORMATION: Reverse primer
```

-continued

```
<400> SEQUENCE: 8
agcctacgac agggaagtgt gac                                              23

<210> SEQ ID NO 9
<211> LENGTH: 23
<212> TYPE: DNA
<213> ORGANISM: Artificial
<220> FEATURE:
<223> OTHER INFORMATION: Reverse primer

<400> SEQUENCE: 9
gcataagaaa aagcggagtt cgg                                              23

<210> SEQ ID NO 10
<211> LENGTH: 21
<212> TYPE: DNA
<213> ORGANISM: Artificial
<220> FEATURE:
<223> OTHER INFORMATION: Reverse primer

<400> SEQUENCE: 10
agacaaaaca ggatgggtgc c                                                21

<210> SEQ ID NO 11
<211> LENGTH: 23
<212> TYPE: DNA
<213> ORGANISM: Artificial
<220> FEATURE:
<223> OTHER INFORMATION: Reverse primer

<400> SEQUENCE: 11
ttgaaggcga cagagatgaa gag                                              23

<210> SEQ ID NO 12
<211> LENGTH: 23
<212> TYPE: DNA
<213> ORGANISM: Artificial
<220> FEATURE:
<223> OTHER INFORMATION: Reverse primer

<400> SEQUENCE: 12
cgtagcagca ccagtggaac ttg                                              23
```

METHOD OF DETERMINATION OF DIAGNOSIS AND PROGNOSIS IN PATIENTS WITH B-CELL CHRONIC LYMPHOCYTIC LEUKEMIA AND OLIGONUCLEOTIDES FOR USE IN THIS METHOD

FIELD OF ART

The invention relates to a method of determination of diagnosis and/or prognosis in patients suffering from B-cell chronic lymphocytic leukemia (CLL) and to oligonucleotides for use in this method.

BACKGROUND ART

B-cell chronic lymphocytic leukemia (CLL) is clinically a very heterogeneous disease with so far unclear pathogenesis. It ensues from the existing knowledge that it is a monoclonal expansion of B-lymphocytes that subsequently gather both in peripheral blood and in lymphatic organs, which further cause life-threatening complications in the form of enlargement of organs, a decreased function of immunity system, anaemia and others. It is supposed that the disease originates in the consequence of disturbance of apoptosis and changes in B lymphocytes migration. In 1975, a first prognostic system according to Rsi (Rai K R, Sawitsky A, Cronkite E P et al.: Clinical staging of chronic lymphocytic leukemia. Blood 1975 46: 219-234) was published and introduced, and subsequently in 1977 a similar classification of the disease according to Binet (Binet J L, Lepoprier M, Dighiero G et al.: A clinical staging system for chronic lymphocytic leukemia: prognostic significance. Cancer. 40, 855-64, 1977; Binet J L, Auquier A, Dighiero G et al.: A new prognostic classification of chronic lymphocytic leukemia derived from a multivariate survival analysis. Cancer 48:198-206, 1981) was introduced. Both systems are based on basic and clinically easy to observe features or available laboratory parameters (number and shape of lymphocytes, thrombocytes, values of haemoglobin, anaemia, infiltration of organs, etc.). In connection with modern molecular markers these systems are still used for the determination of prognosis.

With the introduction of cytogenetic methods, a correlation was observed between certain cytogenetic changes in the cells of patients and the development of their disease. For instance, deletions 17p and 11q are connected with a worse prognosis and, on the contrary, deletion 13q or trisomia of chromosome 12 are considered a positive prognostic feature. On the p arm of chromosome 17, there is located the tumour-suppressor gene p53 and the gene ATM (ataxia teleangiectasia mutated) is located on the q arm of chromosome 11. Both these genes act in the protection of the cell against damaging influences, therefore, their loss or mutation is connected with higher agressiveness of the disease. With regard to the fact that cytogenetic abnormalities occur in 75 to 80% of the patients, the examination by means of FISH probes panel has been included among standard examination procedures.

Another method available at present is the determination of the mutation status of the variable part of immunoglobulin chain by means of sequencing, and this method contributes significantly to the determination of the prognosis of the patients. It has been shown that the mutation status does not change during the disease. The patients with unmutated IgVH have a worse prognosis than those with the mutated one (Hamblin T J, Davis Z, Gardiner A et al.: Unmutated IgVH genes are associated with a more aggressive form of chronic lymphocytic leukemia. Blood 94, 1999, 1848-1854), wherein IgVH with less than 98% homology is considered to be mutated. The mutation status is a significant prognostic indicator regardless of the clinical stage at which the patients are. A significant improvement in the determination of the mutation status and subsequently of the prognosis of the patient was achieved by the recent identification of a molecular prognostic marker, cytoplasmatic protein ZAP-70 (Rosenwald A, Alizadeh A A, Widhopf G et al.: Relation of gene expression phenotype to immunoglobulin mutation genotype in B cell chronic lymphocytic leukemia. J Exp Med 194, 2001, 1639-1647), the high concentration of which correlates significantly with the unmutated IgVH status. Further developments leading to more accurate diagnosis include, e.g., the determination of expression of the surface molecule CD38 that is stable in time and the high expression of which is connected with a worse progression of the disease (Damle R N, Wasil T, Fais F et al.: IgV gene mutation status and CD38 expression as novel prognostic indicators in chronic lymphocytic leukemia. Blood 94, 1999, 1840-1847). Several prognostic markers are known, however, they have not been tested in a larger group of patients yet. A complex use of the above-mentioned analyses contributes significantly to the determination of the prognosis of the patients, however, so far no specific marker is known that would enable to identify with certainty the patients whose disease will prograde in near future and distinguish them from those patients who will remain at the clinical stage for many years without any need for therapy.

The aim of the present invention is to provide a method of determination of the diagnosis and/or prognosis which could replace the current diagnostic and prognostic methods by introducing new and specific markers that will enable the determination of the diagnosis and the prognosis on the basis of the diagnosis. Based on the determined diagnosis and prognosis, the most suitable treatment procedure for each individual patient is selected. The determination of the diagnosis and prognosis can easily be repeated in the course of the disease. Furthermore, the present invention can form a basis for the preparation of targeted therapy at several levels of cell signalization taking account of the current condition of a particular patient.

DISCLOSURE OF THE INVENTION

Object of the present invention is a method for determination of the diagnosis and/or prognosis of B-cell chronic lymphocytic leukemia (CLL) from a biological sample collected from the body of a patient, wherein the status of the signaling pathway Wnt/PCP is determined.

The term "determination of the diagnosis and/or prognosis" as it is used in this description shall be understood as including the determination of the diagnosis of CLL, the determination of the acuity of CLL in the patient, the determination of the prognosis on the basis of the diagnosis, as well as the selection of a suitable treatment.

The term "determination of the status of the signaling pathway" as it is used in this description shall be understood to include the determination of the extent of expression of the signaling pathway components, the up-regulation of the signaling pathway components and/or the determination of the functionality or the activity of the signaling pathway as a whole.

The biological sample collected from the body of the patient is preferably a sample of peripheral blood.

Within the framework of the present invention, the relation between the CLL and the molecular signaling pathway Wnt/PCP, the components of which are significantly up-regulated in B-lymphocytes of the patients with CLL, was identified.

Wnt/planar cell polarity (PCP) is a signaling pathway that was originally described in the drosophila *Drosophila melanogaster* (Seifert J R, Mlodzik M: Frizzled/PCP signalling: a conserved mechanism regulating cell polarity and directed motility. Nat Rev Genet. 2007 February; 8(2):126-38). The components of the Wnt/PCP pathway (the so-called PCP proteins) regulate particularly the cell polarity and orientation. This function was investigated in detail in the regulation of cell orientation in the wing and composite eye of *drosophila*. Only recently, the function of Wnt/PCP pathway was also characterized in vertebrates. In amphibians and mammals it regulates particularly the key cell movements (the so-called morphogenetic movements) in the early embryonic development (especially at the stages of gastrulation and neurulation) and in the adult organisms it regulates the polarity of capillaceous cells in the inner ear (Seifert J R, Mlodzik M: Frizzled/PCP signalling: a conserved mechanism regulating cell polarity and directed motility. Nat Rev Genet. 2007 February; 8(2):126-38; Torban E, Kor C, Gros P: Van Gogh-like2 (Strabismus) and its role in planar cell polarity and convergent extension in vertebrates. Trends Genet. 2004 November; 20(11):570-7). There is not much known about the role of the Wnt/PCP pathway in the pathogenesis of human diseases, with the exception of several findings of an increased or a decreased level of the individual components of this pathway in solid tumours (summarized in Essen J R: Non-canonical Wnt signaling in tumor progression and metastasis, Zebrafish 2009, 6: 1-8). In leukemic diseases, only one case is known so far in which it has been shown that the expression of the secreted ligand Wnt5a of this pathway is decreased in the patients with acute myeloid and acute lymphoblastic leukemia (Liang et al., Wnt5a inhibits B cell proliferation and functions as a tumor suppressor in haematopoietic tissue. Cancer Cell 2003, 4: 349-360). According to the information available to us, no data were available so far about the role of the PCP proteins in CLL.

The key components of the Wnt/PCP pathway include ligands from the family Wnt (especially, Wnt5a and Wnt11) that bind to their membrane receptors from the Frizzled family, further, membrane proteins Van Gogh like 2 (Vangl2; in *Drosophila* called Strabismus) and Celsr1 (in *Drosophila* called Flamengo), cytoplasmatic components Dishevelled (Dvl), Prickle 1, and kinases casein kinase 1 epsilon (CK1ε) and casein kinase 2 alpha (CK2α) (Seifert J R, Mlodzik M: Frizzled/PCP signalling: a conserved mechanism regulating cell polarity and directed motility. Nat Rev Genet. 2007 February; 8(2):126-38; Torban E, Kor C, Gros P: Van Gogh-like2 (Strabismus) and its role in planar cell polarity and convergent extension in vertebrates. Trends Genet. 2004 November; 20(11):570-7).

Our results show that the following parts of the Wnt/PCP pathway are up-regulated in CLL: (i) membrane receptors—Vangl2, Celsr1, Frizzled 3 (Fz3) and Frizzled 7 (Fz7), (ii) cytoplasmatic proteins Dvl 2, Dvl 3 and Prickle1, (iii) kinases casein kinase 1 epsilon (CK1ε) and casein kinase 2 alpha (CK2α) and (iv) secreted ligand of that pathway Wnt5a.

The status of the signaling pathway Wnt/PCP can be determined, e.g., by determining the expression of at least one protein belonging to the signaling pathway Wnt/PCP and/or at least one gene encoding protein belonging to the signaling pathway Wnt/PCP.

Preferably, the protein belonging to the signaling pathway Wnt/PCP is selected from the group comprising membrane receptors Vangl2, Celsr1, Frizzled 3 and Frizzled 7, cytoplasmatic proteins Dvl 2, Dvl 3 and Prickle1, kinases casein kinase 1 epsilon and casein kinase 2 alpha and the secreted ligand of this pathway Wnt5a. The expression of the proteins can be determined, e.g., by the methods Western blotting or ELISA, the expression of the membrane receptors can be determined also by other methods such as flow cytometry.

Preferably, the gene encoding the protein belonging to the signaling pathway Wnt/PCP is selected from the group comprising wnt5a, frizzled 7, frizzled 3, vangl2, prickle1 and celsr1. The expression of the gene encoding the protein can be determined, e.g., by the method of quantitative PCR (real-time PCR).

For the detection of gene expression by the method of quantitative PCR the following oligonucleotides can be used as primers:

| Gene | Forward primer (5' to 3') | Reverse primer (5' to 3') |
|---|---|---|
| celsr1 | TACAACCTTTGGGCTCTGGCTG (SEQ ID NO: 1) | CCTTCATCAGGGTCGTTAGCAC (SEQ ID NO: 7) |
| frizzled3 | TTGAGGATGTGCCAAGATTTGC (SEQ ID NO: 2) | AGCCTACGACAGGGAAGTGTGAC (SEQ ID NO: 8) |
| frizzled7 | TACCACGGAGAGAAGGGCATC (SEQ ID NO: 3) | GCATAAGAAAAAGCGGAGTTCGG (SEQ ID NO: 9) |
| prickle1 | TTCAGTGCTCAGCGGAAGAAAG (SEQ ID NO: 4) | AGACAAAACAGGATGGGTGCC (SEQ ID NO: 10) |
| vangl2 | ACAGTAGTAACGGGCACCTCAGAGC (SEQ ID NO: 5) | TTGAAGGCGACAGAGATGAAGAG (SEQ ID NO: 11) |
| wnt5a | AACAGCCGCTTCAACTCGC (SEQ ID NO: 6) | CGTAGCAGCACCAGTGGAACTTG (SEQ ID NO: 12) |

Oligonucleotides not fully identical with the primers specified herein above can be used, however, they should have at least 75%, preferably at least 85%, homology with the primers specified herein. The decrease of homology to 75% (85%) in comparison with the original sequence of nucleotides can be achieved, e.g., by extension or shortening of the primers by several nucleotides at the 5' and/or 3' end.

The status of the signaling pathway Wnt/PCP can be determined, in another embodiment of the invention, by the determination of migration of CLL cells in a chemokine gradient in the presence of Wnt5a.

It has been shown recently that Wnt5a, the key component of the Wnt/PCP pathway, is essential for cell polarization in the gradient of chemokine (CXCL12) (Witze E S, Litman E S, Argast G M, Moon R T, Ahn N G: Wnt5a control of cell polarity and directional movement by polarized redistribution of adhesion receptors. Science. 2008 Apr. 18; 320(5874): 365-9). This ability of Wnt5a is most probably mediated by the PCP proteins. It is important to mention that chemokines such as CXCL12, CCL19 and CCL21 regulate positively the invasiveness and transendothelial migration of CLL cells and create the gradient between peripheral blood and another different environment that is represented by lymphatic nodes and bone marrow. Our results show the direct effect of the PCP proteins on the migration of, namely, both normal CLL cells and CLL cells in the gradient of chemokine (see below Example 7). We have developed a procedure that enables the testing of the ability of the CLL cells to migrate in the presence and the absence of recombinant Wnt5a (200 ng/ml) using Transwell migration wells (Redondo-Muñoz J, Escobar-Díaz E, Samaniego R, Terol M J, García-Marco J A, García-Pardo A: MMP-9 in B-cell chronic lymphocytic leukemia is up-regulated by alpha4beta1 integrin or CXCR4 engagement via distinct signaling pathways, localizes to podosomes, and is involved in cell invasion and migration. Blood. 2006 Nov. 1; 108(9):3143-51; Richardson S J, Matthews C, Catherwood M A, Alexander H D, Carey B S, Farrugia J, Gardiner A, Mould S, Oscier D, Copplestone J A, Prentice A G: ZAP-70 expression is associated with enhanced ability to respond to migratory and survival signals in B-cell chronic lymphocytic leukemia (CLL). Blood. 2006 May 1; 107(9):3584-92). The extent of the migration of the CLL cells in the chemokine gradient after the stimulation by Wnt5a may be determined, e.g., by the procedure specified in Example 7 and used for the determination of the migration capacity of the CLL cells in vitro. The ability to migrate then closely correlates with the infiltration of lymphatic organs and with the aggressiveness of the disease (Till K J, Lin K, Zuzel M., Cawley J C. The chemokine receptor CCR7 and a4 integrin are important for the migration of chronic lymphocytic leukemia cells into lymph nodes. Blood. 2002 99: 2977-2984).

A further object of the present invention are oligonucleotides having at least 75%, preferably at least 85%, homology of the nucleotide sequence with sequences selected from the group comprising:

| Forward primer (5' to 3') | Reverse primer (5' to 3') |
|---|---|
| TACAACCTTTGGGCTCTGGCTG (SEQ ID NO: 1) | CCTTCATCAGGGTCGTTAGCAC (SEQ ID NO: 7) |
| TTGAGGATGTGCCAAGATTTGC (SEQ ID NO: 2) | AGCCTACGACAGGGAAGTGTGAC (SEQ ID NO: 8) |
| TACCACGGAGAGAAGGGCATC (SEQ ID NO: 3) | GCATAAGAAAAAGCGGAGTTCGG (SEQ ID NO: 9) |
| TTCAGTGCTCAGCGGAAGAAAG (SEQ ID NO: 4) | AGACAAAACAGGATGGGTGCC (SEQ ID NO: 10) |
| ACAGTAGTAACGGGCACCTCAGAGC (SEQ ID NO: 5) | TTGAAGGCGACAGAGATGAAGAG (SEQ ID NO: 11) |
| AACAGCCGCTTCAACTCGC (SEQ ID NO: 6) | CGTAGCAGCACCAGTGGAACTTG (SEQ ID NO: 12) |

Object of the present invention are further these oligonucleotides for use in the method of determination of the diagnosis and/or prognosis of B-cell chronic lymphocytic leukemia according to the present invention.

The contributions of the present invention over the prior art include the identification of a molecular pathway that has not yet been connected in any way with the pathogenesis of CLL. The components of the pathway concerned active in the CLL include both surface molecules and cytoplasmatic proteins, including several kinases.

The determination of the expression of the individual components of the pathway concerned (by means of RT-PCR and flow cytometry in the case of surface markers, or by the method RT-PCR, Western blotting, or ELISA in the case of cytoplasmatic components) will enable the use of the invention as a diagnostic marker.

We show herein that the expression of the components of the Wnt/PCP pathway (hereinafter referred to as PCP proteins) correlates with the progression of CLL, and that the Wnt/PCP pathway regulates the migration of CLL cells. It has been shown that the ability of CLL cells to migrate and infiltrate the secondary lymphatic organs contributes, in principle, to the progression of CLL. It will be possible to apply the invention by way of introduction of new diagnostic markers and of the determination of the migration capacity of CLL cells in a chemokine gradient.

BRIEF DESCRIPTION OF DRAWINGS

FIG. 1 summarizes the results of diagnostics of CLL from mononuclears of peripheral blood by the method RT-PCR according to Example 1.

FIG. 2A shows the results of the analysis of the samples from CLL patients and healthy controls by the method Western blotting. FIG. 2B shows the comparison of the extent of the expression of the proteins in healthy controls, patients with CLL at stages 0-II and patients with CLL at stages III-IV on the scale: non-detectable expression, weak expression, strong expression.

FIG. 6A shows that two groups of patients can be distinguished based on the expression level of the wnt5a gene. FIG. 6B shows Kaplan-Meier survival curve (Treatment Free Survival—TFS) based on the expression of the fz7 gene in a group of CLL patients with a low expression of the wnt5a gene.

SEQUENCE LISTING

SEQ. ID. NO. 1: amino acid sequence of protein Dvl2
SEQ. ID. NO. 2: amino acid sequence of protein Dvl3
SEQ. ID. NO. 3: amino acid sequence of protein CK1ε
SEQ. ID. NO. 4: amino acid sequence of protein CK2α
SEQ. ID. NO. 5: amino acid sequence of protein Vangl2
SEQ. ID. NO. 6: cDNA sequence Wnt5a
SEQ. ID. NO. 7: cDNA sequence Frizzled3 (Fz3)
SEQ. ID. NO. 8: cDNA sequence Frizzled7 (Fz7)
SEQ. ID. NO. 9: cDNA sequence Prickle 1

SEQ. ID. NO. 10: cDNA sequence Vangl2
SEQ. ID. NO. 11: cDNA sequence Celsr1

EXAMPLES OF CARRYING OUT THE INVENTION

Example 1

Diagnostics of C LL from Mononuclears of Peripheral Blood by the Method RT-PCR

Peripheral blood of a CLL patient was transferred to a test tube and the volume of blood was measured. 6 ml of diluted blood were layered to 3 ml of Ficoll-Paque Plus® tempered to laboratory temperature. Centrifugation was performed for 30 minutes/400 g. The layer of lymphocytes was transferred to a clean test tube (15 cm) and completed with 2% FBS (fetal bovine serum in physiological solution with phosphate buffer) to 10 ml, the number of test tubes was selected so that the separated lymphocytes might be diluted at least 2×, the content of the test tubes was thoroughly mixed. After that, centrifugation was performed for 10-15 minutes/200 g, the supernatant was removed and the sediment was suspended in 1 ml of cooled lysing buffer (lysion of erythrocytes—154.9 mM NH4Cl, 9.9 mM NH4HCO3, 1 mM EDTA), the volume was completed to 10 ml and mixed by turning over. Sediments from more test tubes were combined in this step. Centrifugation 10-15 minutes/200 g was performed, supernatant removed and the sediment suspended in 2% FBS and transferred to a test micro-tube. After a further centrifugation 10 minutes/200 g the supernatant was removed and the sediment was lysed in 350 µl RLT buffer (lysing buffer, part of RNeasy Mini Kit of the company Qiagen intended for the isolation of total RNA).

Total RNA was isolated from the separated CLL cells by means of High Pure RNA Isolation Kit according to the instructions of the manufacturer (Roche). The quality and concentrations of the obtained total RNA were determined by spectrophotometry (NanoDrop) and electrophoresis (Bio-Analyzer 2100). Only the samples showing good parameters (RIN>8, Concentration>50 ng/µl) were used for further analysis. The system FastStart Taq DNA Polymerase (Roche) was used for the synthesis of the cDNA according to the instructions of the manufacturer. 500 ng of total RNA were transcribed. The obtained 20 µl cDNA were diluted by RNAse-free water to the final volume of 50 µl. Each sample was analyzed in triplicate by means of the system LightCycler® 480 SYBR Green I Master (Roche), according to the instructions of the manufacturer. The DNA amplification was subsequently detected by the device LightCycler® 480 Real-Time PCR System (Roche) and the obtained data were analyzed by means of the software LightCycler® 480 Software (Roche). The result was the number of the cycle during which the fluorescence achieves a pre-set threshold (Ct—fluorescence threshold cycle). The relative expression of the gene was normalized to the expression of the operating gene GAPDH (ΔCt). The obtained data were analyzed by means of non-parametric Wilcox test.

Figure 1A:
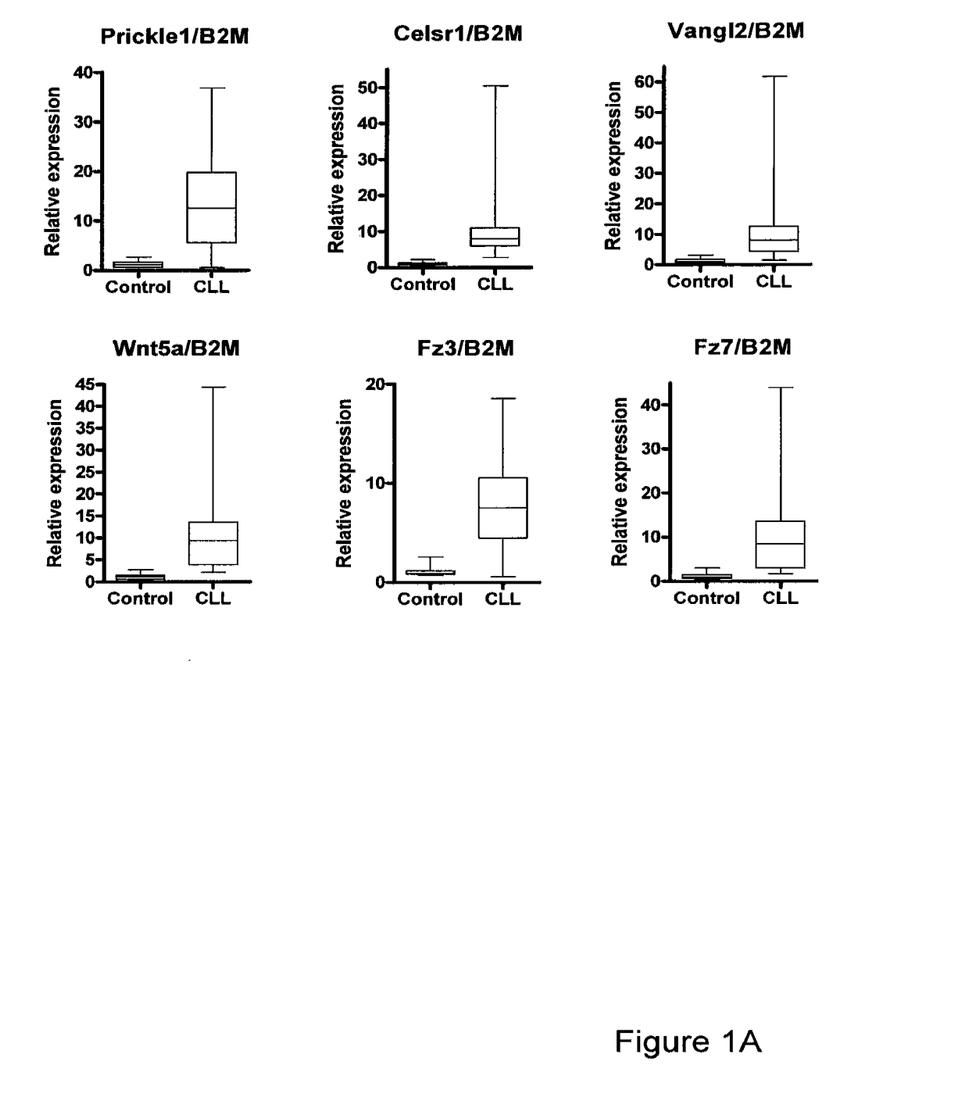
FIG. 1A summarizes the relative expression of a set of tested genes in relation to an endogenic control B2M (Beta-2 microglobulin) in mononuclears of 14 controls and 25 patients with CLL.

In the subsequent step we obtained samples from mononuclears of peripheral blood both of healthy controls and of patients at clinical stages 0-IV according to Rai, and we analyzed the expression of human homologues of the genes that are associated with non-canonical Wnt signalization (particularly the Wnt/PCP pathway). The expression of the genes prickle1, vangl2, celsr1, wnt5a, frizzled3 and frizzled7 and endogenous controls (B2M and actin) was determined by means of RT-PCR. We analyzed the expression in a panel of patients at various clinical stages according to Rai. FIG. 1A summarizes the expression of these genes in mononuclears of 14 controls and 25 patients. The results of quantitative real time-PCR (qRT-PCR) analysis provide the evidence that some PCP genes are highly expressed at the level of transcription in CLL cells.

Figure 1B:
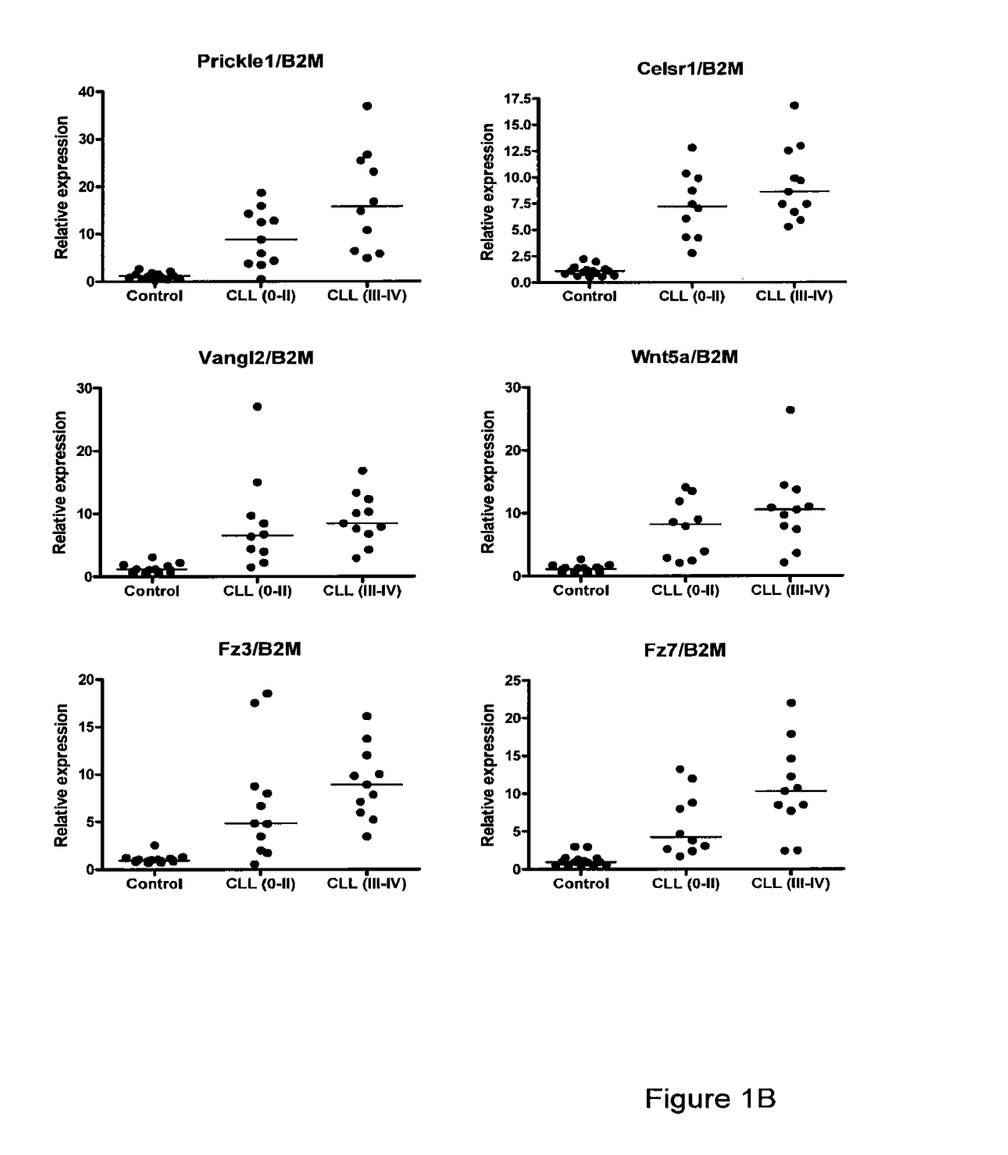
FIG. 1B shows the correlation of the expression of the markers with the stages of CLL.

During qRT-PCR and the analysis of the protein expression we detected considerable variability in the expression of the individual markers. This is why we tested the possibility that the expression of PCP genes is associated with the progression of CLL. Therefore, we classified the patients according to the clinical stage (according to Rai), namely, into categories (i) stage 0-II and (ii) stage III-IV. As shown in FIG. 1B, the expression of the majority of the markers determined by RT-PCR correlates with the stages of CLL. These trends are obvious in all genes, but the differences in the expression of the markers of the CLL patients at the stages 0-II and III-IV in our samples are statistically significant, especially, with prickle1 and frizzled7 (One way ANOVA, Tukey post test, $p<0.05$).

Example 2

Diagnostics of CLL from B-lymphocytes of Peripheral Blood by Means of Quantitative RT-PCR Peripheral blood of the patient suffering from CLL was collected to collection test tubes with anticoagulation substance (heparin). Mononuclear cells were separated by means of gradient centrifugation (Ficoll-Paque PLUS, GE Healthcare) which was preceded by incubation with a cocktail of bispecific antibodies (at one end anti CD2, CD3, CD16, CD36, CD56, CD66b and at the other end anti-glycophorin A) (RosetteSep® B Cell Enrichment Cocktail, StemCell). Undesirable cells form, by means of bispecific antibodies, together with erythrocytes, formations called rosettes.

The density of the formed rosettes is higher than the density of the individual undesirable cells and during gradient centrifugation their sedimentation occurs. Total RNA was isolated from the separated CLL cells by means of High Pure RNA Isolation Kit according to the instructions of the manufacturer (Roche). The quality and the concentration of the obtained total RNA were determined by spectrophotometry (NanoDrop) and electrophoretically (BioAnalyzer 2100). Only the samples with good parameters (RIN>8, concentration>50 ng/µl) were used for further analyses. The system FastStart Taq DNA Polymerase (Roche) was used for the synthesis of cDNA according to the instructions of the manufacturer. 500 ng of total RNA were transcribed. The obtained 20 µl of cDNA were diluted by RNAse-free water to the final volume of 50 µl. Each sample was analyzed in triplicate by means of the system LightCycler® 480 SYBR Green I Master (Roche), according to the instructions of the manufacturer. DNA amplification was subsequently detected by the device LightCycler® 480 Real-Time PCR System (Roche) and the obtained data were analyzed by means of software LightCycler® 480 Software (Roche). The result was the number of the cycle in which the fluorescence achieves a pre-set threshold (CT—fluorescence threshold cycle). The relative expression of the gene was normalized to the expression of the operating gene GAPDH that was selected on the basis of the stability of its expression across the samples.

Example 3

Diagnostics of CLL from B-lymphocytes of Peripheral Blood by Means of Quantitative RT-PCR Peripheral blood of a CLL patient was transferred to a test tube and the volume of the blood was measured. Further, RosetteSep® Human B Cell Enrichment Cocktail (50 µl/ml of blood) was added, the mixture was mixed by circling and incubated for 20 minutes at laboratory temperature. After that at least the same volume of 2% FBS (fetal bovine serum in physiological solution with phosphate buffer) was added, mixed and 6 ml of the diluted blood were layered on 3 ml Ficoll-Paque Plus® tempered to laboratory temperature. Centrifugation was performed 30 minutes/400 g. The layer of lymphocytes was transferred to a clean test tube (15 cm) and completed with 2% FBS to 10 ml, the number of test tubes was selected so that the separated lymphocytes might be diluted at least 2x, the content of the test tubes was thoroughly mixed. After that, centrifugation was performed 10-15 minutes/200 g, the supernatant was removed and the sediment suspended in 1 ml of cooled lysing buffer (lysion of erythrocytes—154.9 mM NH4Cl, 9.9 mM NH4HCO3, 1 mM EDTA), the volume was completed to 10 ml and mixed by turning over. Sediments from several test tubes were combined in this step. Centrifugation was performed 10-15 minutes/200 g, the supernant was removed and the sediment was suspended in 2% FBS and transferred to a test micro-tube. After further centrifugation 10 minutes/200 g the supernant was removed and the sediment lysed in 350 µl RLT buffer (lysing buffer, a part of RNeasy Mini Kit of the company Qiagen intended for the isolation of total RNA).

Total RNA was isolated from the separated CLL cells by means of High Pure RNA Isolation Kit according to the instructions of the manufacturer (Roche). The quality and concentration of the obtained total RNA was determined spectrophotometrically (NanoDrop) and electrophoretically (BioAnalyzer 2100). Only the samples having good parameters were used for further analyses (RIN>8, concentration>50 ng/µl). FastStart Taq DNA Polymerase system (Roche) was used for the synthesis of cDNA according to the instructions of the manufacturer. 500 ng of total RNA were transcribed. The obtained 20 µl of cDNA were dissolved by RNAse-free water to the final volume of 50 µl. Each sample was analyzed in triplicate by means of the system LightCycler® 480 SYBR Green I Master (Roche) according to the instructions of the manufacturer. The DNA amplification was detected subsequently by the device LightCycler® 480 Real-Time PCR System (Roche) and the obtained data were analyzed by means of software LightCycler® 480 Software (Roche). The result was the number of the cycle during which the fluorescence achieves a pre-set threshold (Ct—fluorescence threshold cycle). The relative expression of the gene was normalized to the expression of the operating gene GAPDH (ΔCt). The obtained data were analyzed by means of non-parametric Wilcoxon test.

The following primers were used for the detection of gene expression in examples 1-3.

| Gene | Forward primer (5' to 3') | Reverse primer (5' to 3') | Prod (bp) |
|---|---|---|---|
| celsr1 | TACAACCTTTGGGCTCTGGCTG (SEQ ID NO: 1) | CCTTCATCAGGGTCGTTAGCAC (SEQ ID NO: 7) | 197 |
| frizzled3 | TTGAGGATGTGCCAAGATTTGC (SEQ ID NO: 2) | AGCCTACGACAGGGAAGTGTGAC (SEQ ID NO: 8) | 209 |
| frizzled7 | TACCACGGAGAGAAGGGCATC (SEQ ID NO: 3) | GCATAAGAAAAAGCGGAGTTCGG (SEQ ID NO: 9) | 207 |
| prickle1 | TTCAGTGCTCAGCGGAAGAAAG (SEQ ID NO: 4) | AGACAAAACAGGATGGGTGCC (SEQ ID NO: 10) | 175 |
| vangl2 | ACAGTAGTAACGGGCACCTCAGAGC (SEQ ID NO: 5) | TTGAAGGCGACAGAGATGAAGAG (SEQ ID NO: 11) | 248 |
| wnt5a | AACAGCCGCTTCAACTCGC (SEQ ID NO: 6) | CGTAGCAGCACCAGTGGAACTTG (SEQ ID NO: 12) | 232 |

Example 4

Diagnostics of CLL from Mononuclears of Peripheral Blood by Means of the Method Western Blotting Peripheral blood of a CLL patient was transferred to a test tube and the volume of the blood was measured. 6 ml of the dissolved blood were layered on 3 ml Ficoll-Paque Plus® tempered to laboratory temperature. Centrifugation was performed 30 minutes/400 g. The layer of lymphocytes was transferred to a clean test tube (15 cm) and completed with 2% FBS to 10 ml, the number of the test tubes was selected so that the separated lymphocytes might be diluted at least 2x, the content of the test tubes was thoroughly mixed. After that, centrifugation was performed 10-15 minutes/200 g, the supernant was extracted and the sediment suspended in 1 ml of cooled lysing buffer (lysion of erythrocytes—154.9 mM NH4Cl, 9.9 mM NH4HCO3, 1 mM EDTA), the volume was completed to 10 ml and mixed by turning over. Sediments from several test tubes were combined in this step. Centrifugation was performed 10-15 minutes/200 g, the supernatant extracted and the sediment suspended in 2% FBS and transferred to a test micro-tube. After further centrifugation 10 minutes/200 g the supernant was extracted and the sediment was lysed in lysing buffer (0.5% NP-40, 150 mM NaCl, 50 mM Tris pH 7.4, 1 mM EDTA). After sonication (Branson Sonifier 150), the quantity of proteins was determined by means of Bio-Rad DC Protein Assay kit. The samples were adjusted to the unified concentration of proteins 1 µg/µl, and 20 µl of each sample were applied on 8% polyacrylamide gel and analyzed by the method SDS-PAGE/Western blotting according to standard procedure using polyvinylidenedifluoride (PVDF) membranes (Towbin H, Staehelin T, Gordon J. (1979): Electrophoretic transfer of proteins from polyacrylamide gels to nitrocellulose sheets: procedure and some applications. *Proc Natl Acad Sci USA*. 76 (9): 4350-4354; Pluskal M G, Przekop M B, Kavonian M R, Vecoli C, Hicks D A, Immobilon PVDF transfer membrane: A new membrane substrate for Western blotting of proteins. *BioTechniques* 4, 1986, pp. 272-282). After blotting, the membranes were blocked for 1 hr. in 5% non-fat milk (Promil, Laktino) in TBS-Tween (100 mM NaCl, 20 mM Tris (pH 7,6), 0.05% Tween 20, dissolved in distilled water pH 7.1-7.2)

The following combinations of antibodies diluted in 5% milk/TBS-Tween were used for the detection:

| antigen | Primary antibody (manufacturer) | Dilution of primary antibody | Secondary antibody (manufacturer) | Dilution of secondary antibody |
|---|---|---|---|---|
| Dvl2 | #3224 anti-rabbit Dvl2 (Cell Signaling Technology) | 1:1000 | A6667 anti-rabbit IgG (Sigma-Aldrich®) | 1:5000 |
| Dvl3 | SC-8027 anti-mouse Dvl3 (Santa Cruz Biotechnology, inc) | 1:500 | A6782 anti-mouse IgG (Sigma-Aldrich®) | 1:5000 |
| Casein kinase 1 ε (CK1ε) | SC-6471 anti-goat CK1 (Santa Cruz Biotechnology, inc.) | 1:500 | A4174 anti-goat IgG (Sigma-Aldrich®) | 1:5000 |
| Casein kinase 2 α/α' | BD 611611 anti-mouse CK2 (BD Transduction Laboratories™) | 1:500 | A6782 anti-mouse IgG (Sigma-Aldrich®) | 1:5000 |
| Vangl2 | AF 4815 anti-goat Vangl2 (R&D Systems®) | 1:1000 | A4174 anti-goat IgG (Sigma-Aldrich®) | 1:5000 |
| Prickle1 | ab15577 anti-rabbit Prickle1 (Abcam®) | 1:500 | A6667 anti-rabbit IgG (Sigma-Aldrich®) | 1:5000 |
| Actin | SC-1615 anti-rabbit Actin (Santa Cruz Biotechnology, inc.) | 1:5000 | A6667 anti-rabbit IgG (Sigma-Aldrich®) | 1:5000 |

Figure 2:
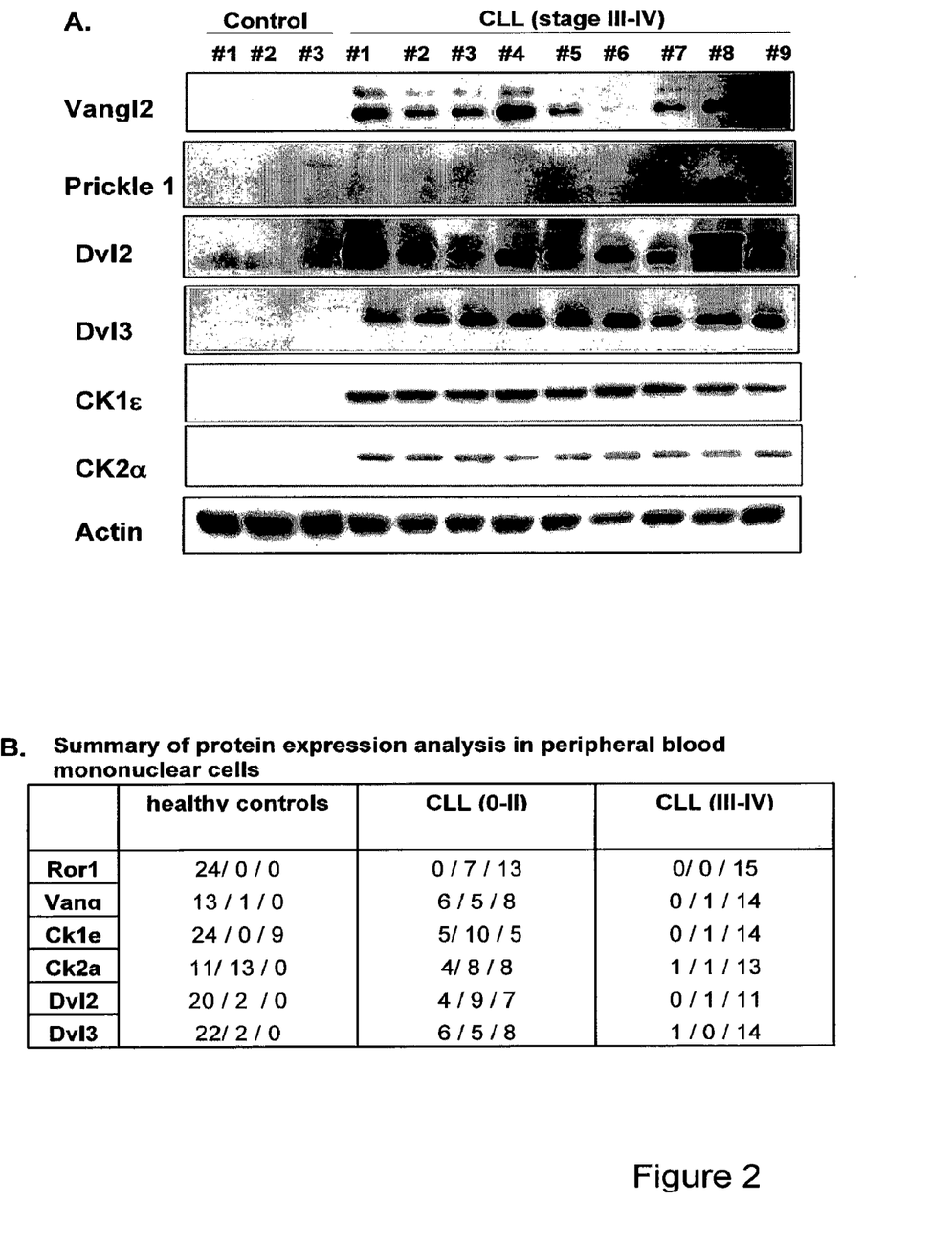
FIG. 2 summarizes the results of diagnostics of CLL from mononuclears of peripheral blood by the method Western blotting according to Example 4.

We present the analysis of the samples of 15 CLL patients and 15 healthy controls by the method Western blotting and the obtained data in FIG. 2A. Increased levels of PCP proteins, such as Vangl2 and Prickle1, were detected, identified by means of qRT-PCR. It provides evidence that the increased levels of transcripts are transcribed to proteins the increased quantity of which can be detected by this method. The protein analysis of the other components of non-canonical Wnt signalling, such as Dvl2, Dvl3, CK1ε and CK2α, showed a significantly higher levels of those mediators in CLL patients. It is interesting that the transcripts encoding Dvl2 and Dvl3, and CK1ε and CK2α were not demonstrably higher in the primary analysis of mononuclears in CLL patients which means that the level of those proteins is regulated post-transcriptionally.

Because the WB analysis does not provide numerical data, we classified the data to 3 categories only: non-detectable expression, weak expression, strong expression. The summary of this analysis is in FIG. 2B. CK1ε has never been detected in healthy controls, Vangl2, Dvl2 and Dvl3 were detected in the healthy individuals only rarely (less than 10% of examples showed weak expression only) and CK2α was detected weakly in 50% of examples. In the samples of peripheral blood of the patients at stages 0-II protein levels in Dvl2, Dvl3, Vangl2, Ck1ε and CK2α differed from a non-detected signal to a strong signal (roughly by one third). The patients at stages III-IV showed a strong expression of all above-mentioned PCP proteins with the exception of very few patients only. Based on these results, we can conclude that the accumulation of PCP proteins and their transcripts occurs with the progression of CLL.

Example 5

Diagnostics of CLL of B-lymphocytes of Peripheral Blood by Means of the Method Western Blotting Peripheral blood of a CLL patient was transferred to test tubes and the volume of the blood was measured. Rosette-Sep® Human B Cell Enrichment Cocktail (500 ml of blood) was further added, the mixture was mixed by turning over and incubated for 20 minutes at laboratory temperature. After that minimally the same volume of 2% FBS (fetal bovine serum in physiological solution with phosphate buffer) was added, the solutions were stirred and 6 ml of diluted blood was layered on 3 ml Ficoll-Paque Plus® tempered to laboratory temperature. Centrifugation 30 minutes/400 g was performed. The layer of lymphocytes was transferred to a clean test tube (15 cm) and completed with 2% FBS to 10 ml, the number of test tubes was selected so that the separated lymphocytes might be diluted at least 2×, the content of the test tubes was thoroughly mixed. After that, centrifugation 10-15 minutes/200 g was performed, the supernant was extracted and the sediment suspended in 1 ml of cooled lysing buffer (lysion of erythrocytes—154.9 mM NH4Cl, 9.9 mM NH4HCO3, 1 mM EDTA), the volume was completed to 10 ml and mixed by turning over. The sediments from several test tubes were combined in this step. Centrifugation 10-15 minutes/200 g was performed, the supernatant extracted and the sediment suspended in 2% FBS and transferred to a test micro-tube. After further centrifugation 10 minutes/200 g the supernatant was extracted and the sediment lysed and processed in the same manner as in Example 5.

Figure 3:
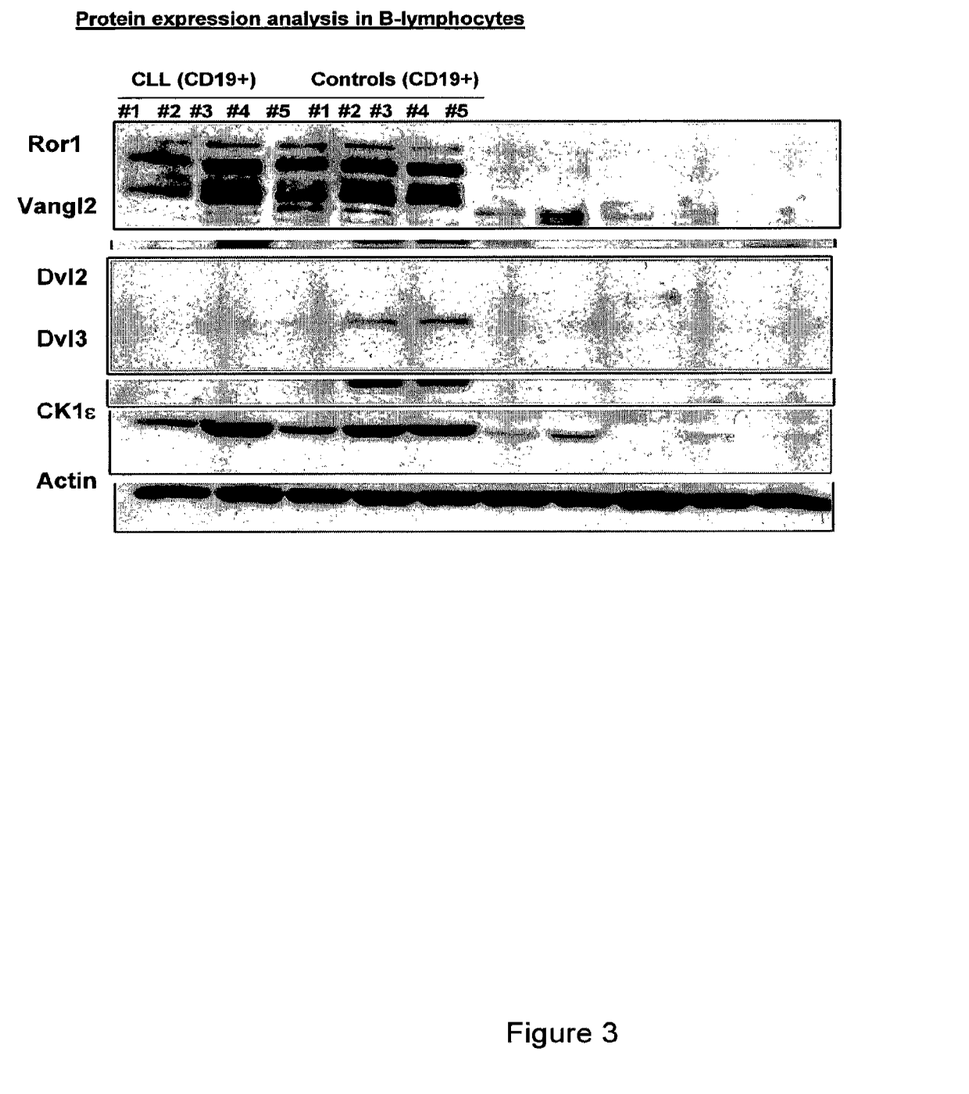
FIG. 3 summarizes the results of diagnostics of CLL from B-lymphocytes of peripheral blood by the method Western blotting according to Example 5—results of the analyses of samples from CLL patients and healthy controls.

The procedure in Example 5 enables us to differentiate whether there is an increased quantity of the PCP proteins directly in the CLL cells or whether it is caused by a contamination by other cell types. The up-regulation of the PCP proteins may be in principle specific for the CLL cells or may reflect the enrichment of peripheral mononuclears of the patients with B-cells. To disprove the second possibility we analyzed the protein levels of Vangl2, Dvl2, Dvl3, Ck1ε and CK2α in formulas after the separation by means of Rosette-Sep Human B Cell Enrichment Cocktail in 5 controls and 5 patients and we obtained similar results as in the non-separated analyzed samples. The percentage of CD19+ cells in all analyzed separated samples was determined at 95% by FACS method. The results are shown in FIG. 3.

Example 6

Determination of the Presence of PCP Proteins on the Surface of CLL Cells

Some PCP proteins are membrane proteins and therefore they are suitable for detection by means of flow cytometry. Therefore, we tested their expression in CD19+ B-cells.

Procedure: Peripheral blood of a CLL patient was transferred to a test tube and the volume of the blood was measured. RosetteSep® Human B Cell Enrichment Cocktail (50 µl/ml of blood) was added, the mixture was mixed by turning over and incubated for 20 minutes at laboratory temperature. At least the same volume of 2% FBS (fetal bovine serum in physiological solution with phosphate buffer) was then added, the mixture was stirred and 6 ml of the diluted blood layered on 3 ml Ficoll-Paque Plus® tempered to laboratory temperature. Centrifugation 30 minutes/400 g was performed. The layer of lymphocytes was transferred to a clean test tube (15 cm) and completed with 2% FBS to 10 ml, the number of test tubes was selected so that the separated lymphocytes might be diluted at least 2x, the content of the test tubes was thoroughly mixed. After that, centrifugation 10-15 minutes/200 g was performed, the supernatant was extracted and the sediment suspended in 1 ml of cooled lysing buffer (lysion of erythrocytes—154.9 mM NH4Cl, 9.9 mM NH4HCO3, 1 mM EDTA), the volume was completed to 10 ml and mixed by turning over. The sediments from several test tubes were combined in this step. Centrifugation 10-15 minutes/200 g was performed, the supernatant extracted and the sediment suspended in 2% FBS and transferred to a test micro-tube. After a further centrifugation 10 minutes/200 g the supernant was extracted, the sediment was washed with 1 ml PBS and after a further centrifugation suspended in a smaller quantity of PBS and fixed in 1 ml of cooled methanol (−20° C.). After fixation in ice-cold methanol the samples were washed in azide buffer (PBS, 1% BSA, 0.1% sodium azide) and centrifuged (200 g/5 min/RT). Each sample was diluted so that it might contain minimum $0.5 \times 10^6$ cells. After adding 50 µl of azide buffer with primary antibody in the ratio 1:50, the samples were incubated at least 1 hr at the temperature of 37° C. The samples were washed in azide buffer, centrifuged and left in 50 µl of azide buffer to which secondary antibody (anti-goat-Cy5 from Jackson ImmunoResearch 1:200, or anti-rabbit-alexa488 from Axxora 1:1000 or anti-mouse-alexa488 from Axxora 1:1000) was added. The samples were incubated for 1 hr at the temperature of 37° C. The measurement was performed with the device FACSCalibur (Becton Dickinson) and CellQuest 3.0 software was used for the assessment (Becton Dickinson).

Figure 4:
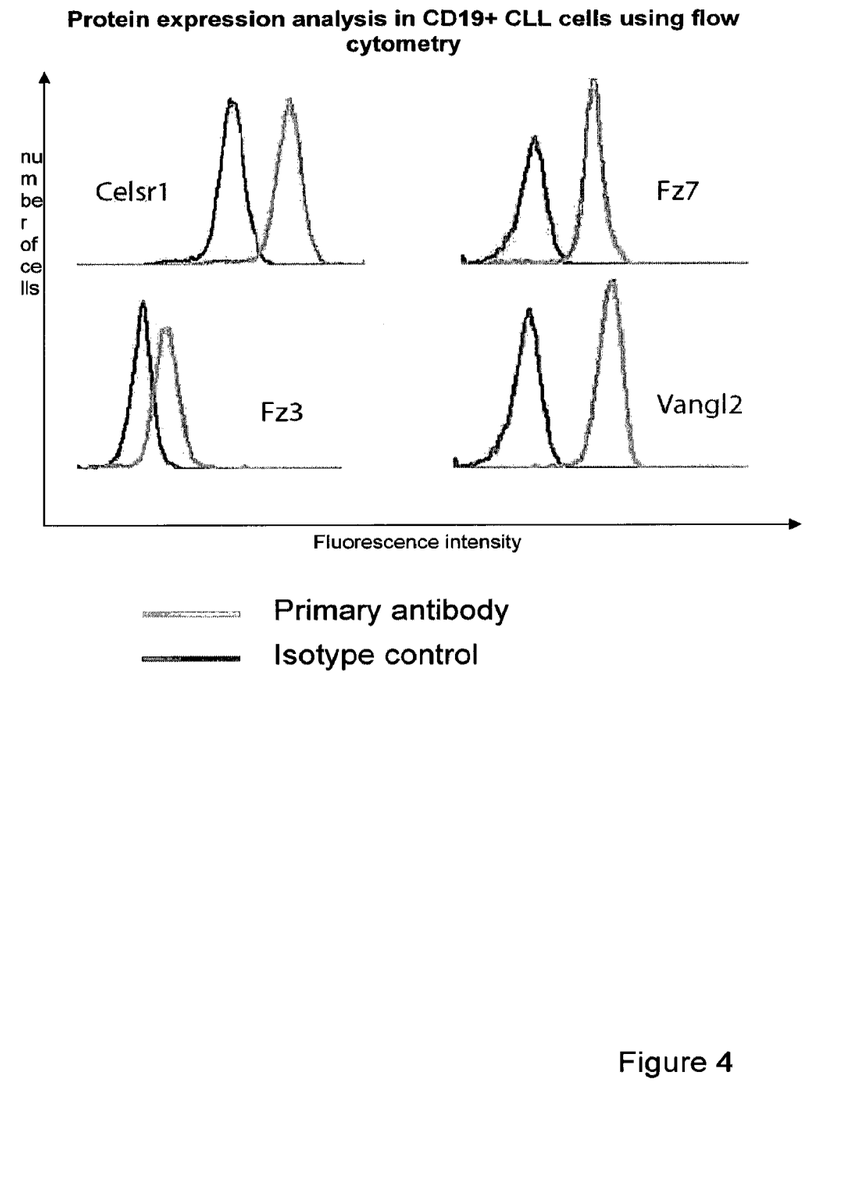
FIG. 4 shows the method of diagnostics of CLL from B-lymphocytes of peripheral blood by the method of flow cytometry according to Example 6.

We present the results in FIG. 4. These results prove, using several methods, that the PCP proteins are up-regulated in CLL leukemic clones in comparison with B-cells of healthy controls and that they are present on the surface of CLL lymphocytes.

Example 7

Determination of Migration of CLL Cells by Means of Transwell Assay

Figure 5:
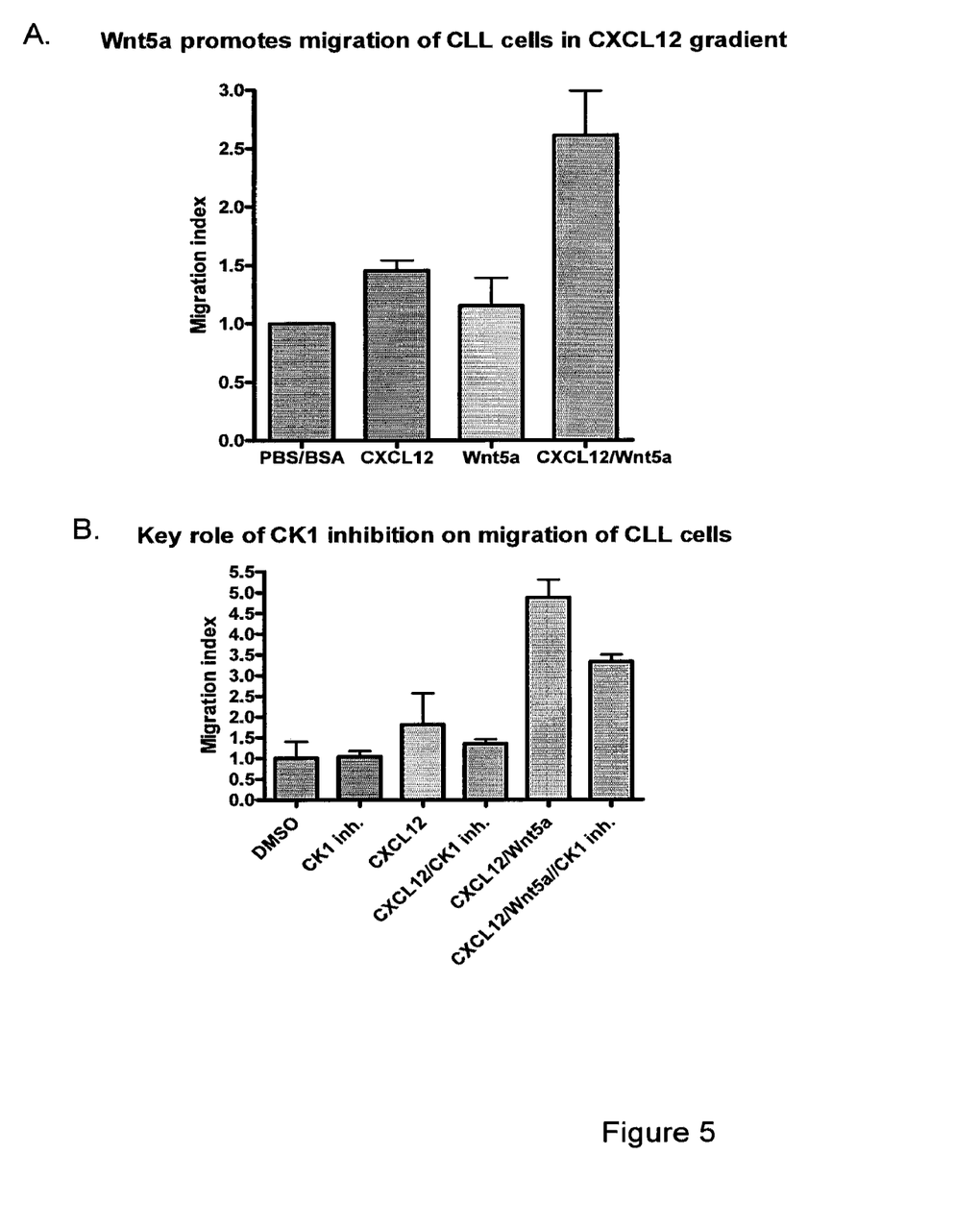
FIG. 5 shows the results of the migration essay according to Example 7. In part A it shows that Wnt5a is able to positively affect the migration of CLL cells in the presence of the chemokine CXCL12, in part B it shows that essential for these effects is the component of the Wnt/PCP pathway CK1 (addition of CK1 inhibitor—D4476, 100 uM—blocks migration).

To prove the direct effect of the PCP proteins on the migration of both normal CLL cells, and CLL cells in the gradient of chemokine, we tested the ability of CLL cells to migrate in the presence and the absence of recombinant Wnt5a (200 ng/ml) using Transwell migration wells (Redondo-Muñoz J, Escobar-Díaz E, Samaniego R, Terol M J, García-Marco J A, García-Pardo A: MMP-9 in B-cell chronic lymphocytic leukemia is up-regulated by alpha4beta1 integrin or CXCR4 engagement via distinct signaling pathways, localizes to podosomes, and is involved in cell invasion and migration. Blood. 2006 Nov. 1; 108(9):3143-51; Richardson S J, Matthews C, Catherwood M A, Alexander H D, Carey B S, Farrugia J, Gardiner A, Mould S, Oscier D, Copplestone J A, Prentice A G: ZAP-70 expression is associated with enhanced ability to respond to migratory and survival signals in B-cell chronic lymphocytic leukemia (CLL). Blood. 2006 May 1; 107(9):3584-92). As we show in FIG. 5A, CXCL12 itself influences positively the migration of CLL cells, while Wnt-5a itself was not able to induce migration. The combination of CXCL12 and Wnt5a significantly increased the migration of CLL in Transwell assay in comparison with other experimental conditions. These data show that Wnt5a induces a better migration of CLL cells to the source of the chemokine CXCL12. To prove that the migration of CLL cells in the chemokine gradient is mediated by the PCP proteins specifically increased in CLL, we inhibited pharmacologically CK1ε. CK1ε is the key component of the Wnt/PCP pathway and its quantity in the patients suffering from CLL is increased. As we show in FIG. 5B, the inhibition of CK1ε blocks the effects of Wnt5a on cell migration in the chemokine gradient. These results demonstrate that the migration of CLL cells is under the control of the PCP proteins and that the pharmacological intervention with the Wnt/PCP pathway blocks their migration which is a property inseparably connected with the progression of CLL. The extent of the migration of CLL cells in chemokine gradient after Wnt5a stimulation may be determined by the following procedure and used for the determination of the migration capacity of CLL cells that correlates closely with the infiltration of lymphatic organs and the agressiveness of the disease (Till K J, Lin K, Zuzel M., Cawley J C. The chemokine receptor CCR7 and a4 integrin are important for migration of chronic lymphocytic leukemia cells into lymph nodes. Blood. 2002 99: 2977-2984).

Procedure:

CLL cells were isolated by the identical procedure as in Example 6. After isolation the cells were transferred to tissue culture and subjected to Transwell assay. 96 well plates were used for the experiments (Corning, HTS Transwell®-96 Permeable Support with 5.0 µm Pore Polycarbonate Membrane). These plates consist of a bottom part including the wells and a top part that includes the inserts, the bottom of which is formed by the membrane of a defined size of pores. Each sample was measured in triplicate. The wells in the bottom part of the plate always included 0.235 ml of the medium (RPMI 1640, 0.1% FBS, 1% Penicillin Streptomycin, 1% L-glutamine) and further the required concentration of the chemokine or solvent (0.1% BSA in PBS). The inserts that contained always 0.08 ml of the medium together with 0.5× $10^6$ cells (it is necessary to the cell suspension to be homogeneous) were inserted subsequently to the plates. Antibodies, solvents and Wnt5a at required concentrations were added to these inserts in parallel. The cultivation was performed in an incubator at 37° C. and 5% $CO_2$ for the period of 20 hours. After the cultivation the inserts were removed from the transwell plate, trypsin was added to each well (100 μl) and after 5 minutes of its activity the number of the cells that migrated through the membrane were counted in each well. The Coulter Counter device, model FN, was used for counting the cells but also Bürker chamber or FACS can be used.

Example 8

Patient Prognosis Based on PCP Gene Expression from the Peripheral Blood Sample of CLL Patient Procedure: Peripheral blood of a CLL patient was transferred into a test tube and the volume of the blood was measured. RosetteSep® Human B Cell Enrichment Cocktail (50 μl/ml blood) was added to the blood sample and the mixture was mixed gently, and incubated for 20 minutes at the room temperature. At least the same volume of 2% FBS (fetal bovine serum in physiological solution with phosphate buffer) was added. After mixing, 6 ml of the diluted blood was transferred on the 3 ml layer of Ficoll-Paque Plus® tempered at room temperature, and spinned down for 30 min at 400 g.

The layer of B-lymphocytes was transferred into a new tube (15 cm) and filled with 2% FBS to 10 ml. The volume of the separated B-lymphocytes was diluted at least twice and was mixed properly. After centrifugation for 10-15 minutes at 200 g, the supernatant was removed and the sediment was first resuspended in 1 ml and then filled up to 10 ml by cooled lysis buffer (for lysis of erytrocytes—154.9 mM NH4Cl, 9.9 mM NH4HCO3, 1 mM EDTA). After this step, sediments of all tubes were put together and centrifuged for 10 min at 200 g. The supernatant was removed and the sediment was resuspended in 2% FBS and transferred to the microtube. After additional centrifugation for 10 min at 200 g, the supernatant was removed and the sediment was lysed in 350 ul of RLT buffer (lysis buffer from Rneasy Mini Kit, Qiagen, for isolation of total RNA). Total RNA from separated CLL B-lymphocytes was isolated using High Pure Isolation Kit according to the manufacturer instructions (Roche). The quality and concentration of isolated total RNA was determined spectrophotometrically (Nanodrop) and eletrophoretically (BioAnalyzer 2100). For next analysis only samples with good parametres were used (RIN>8, concentration>50 ng/μl).

For synthesis of cDNA, the FastStart Taq DNA Polymerase system (Roche) was used according to manufacturer instructions. 500 ng of total RNA was transcribed. Acquired 20u1 of cDNA was diluted with RNAse-free water to the volume of 50 μl. Each sample was analyzed in triplicate using the LightCycler® 480 SYBR Green I Master (Roche) system according to the manufacturer instructions. Subsequently, the amplification of DNA was detected using LightCycler® 480 Real-Time PCR System (Roche) and obtained data were analyzed using LightCycler® 480 Software (Roche). The result was the number of cycle, in which the fluorescence reached adjusted threshold (fluorescence threshold cycle). Relative gene expression was normalized to the expression of the house-keeping gene GAPDH (ΔCt).

Primers from the Example 3 were used for the detection of gene expression. The expression data have been obtained from 61 patients in clinical stages 0-IV. According to the expression level of wnt5a gene, patients were divided into two groups. First group "low wnt5a" was formed by patients with the Wnt5a expression less than 50-fold of average healthy CD19+ B-cells. Second group "high wnt5a" was formed by patients with the wnt5a expression more than 50-fold greater than in average healthy CD19+ B-cells.

Figure 6:
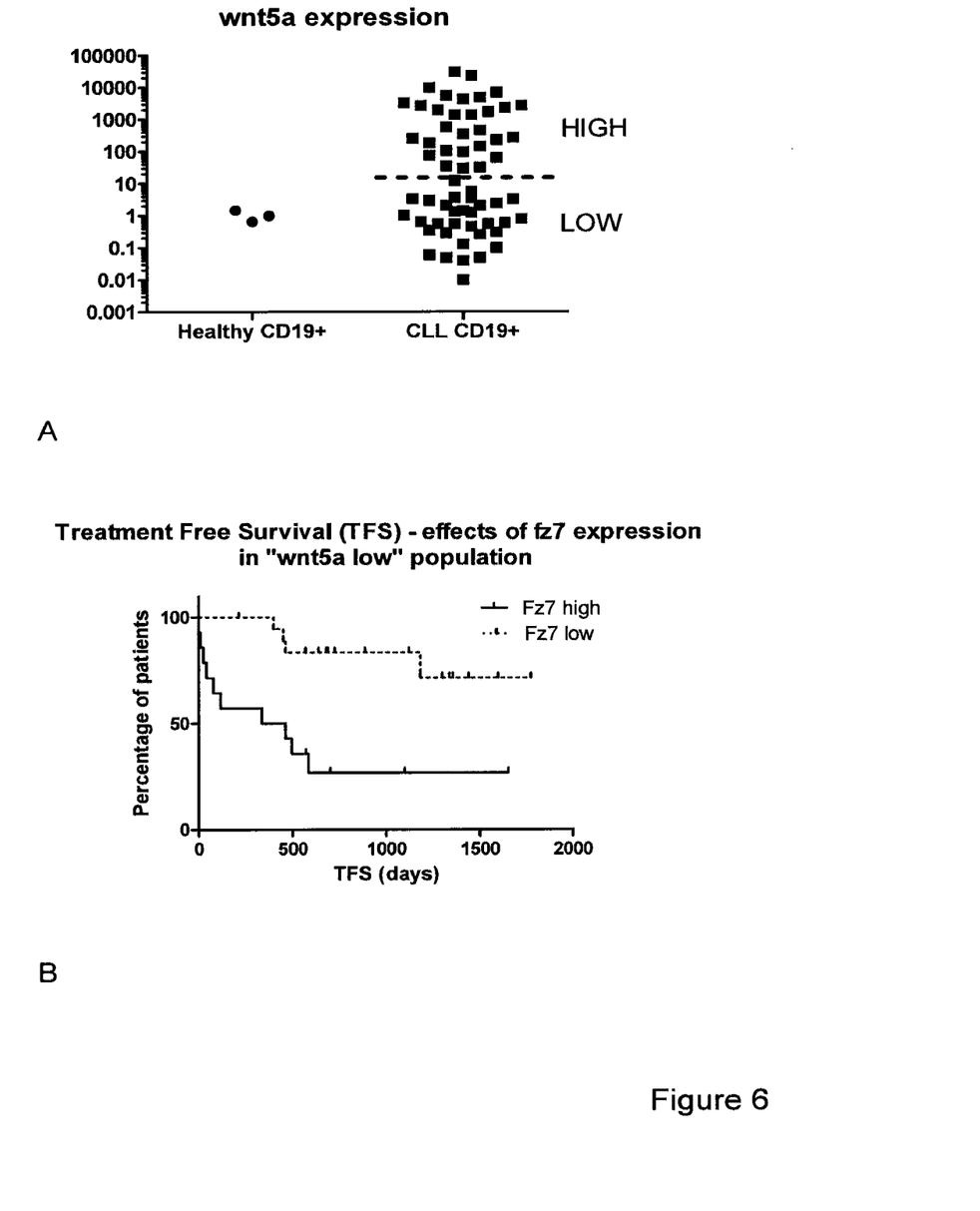
FIG. 6 presents results from qRT-PCR analysis performed on a group of CLL patients.

In FIG. 6A, Y axis represents group of 3 healthy donnors and a group of 61 patients with different disease progression. X axis represents logarithmic scale of wnt5a gene expression. Based on this result, patients were divided into two groups according to the wnt5a expression level. First group "low wnt5a" was formed by patients with the wnt5a expression value less than or equal to 50 on the logarithmic scale. Second group "high wnt5a" was formed by patients with the wnt5a expression value greater than 50 on the logarithmic scale.

Based on the division of patients according to the wnt5a expression level, additional marker from the list of PCP genes can be used for the prognosis assesment in the "wnt5a-low" group. FIG. 6B presents Kaplan-Meier survival curves, which show the statistically significant shorter treatment free survival time in the patients with higher fz7 gene expression in a subset of patients with low wnt5a levels. X axis represents percentage of patients and Y axis represents treatment free survival in days. PCP gene expression level, when combined with the division of patients according to their wnt5a expression level, enabled to assess the prognosis of CLL.

Industrial Applicability

The present invention can be used in diagnostics and treatment of B-cell chronic lymphocytic leukemia (CLL). With regard to the fact that the components of the Wnt/PCP signaling pathway described here are up-regulated in CLL and their expression in adult human tissues is relatively low, the determination of the expression of PCP proteins can be used as diagnostic/prognostic markers.

The invention claimed is:

1. A method of determination of the diagnosis and prognosis of B-cell chronic lymphocytic leukemia, comprising the steps of:

collecting a biological sample containing B-lymphocytes from the body of a patient; and detecting in the biological sample the expression level for all of the proteins in the group consisting of Vangl2, Celsr1, Frizzled 7, Dvl 2, Dvl 3, Prickle1, casein kinase 1 epsilon, casein kinase 2 alpha, and Wnt5a.

2. The method according to claim 1, wherein the biological sample containing B-lymphocytes collected from the body of the patient is a sample of peripheral blood.

3. The method according to claim 1, wherein the expression level is determined by a method selected from the group consisting of Western blotting and ELISA.

* * * * *